US012569467B2

(12) United States Patent
McConnell et al.

(10) Patent No.: US 12,569,467 B2
(45) Date of Patent: Mar. 10, 2026

(54) SMALL MOLECULES THAT TREAT OR PREVENT VIRAL INFECTIONS

(71) Applicant: UNIVERSITY OF HOUSTON SYSTEM, Houston, TX (US)

(72) Inventors: Bradley K. McConnell, Houston, TX (US); Arfaxad Reyes Alcaraz, Houston, TX (US); John W. Craft, Houston, TX (US); Robert J. Schwartz, Houston, TX (US)

(73) Assignee: University of Houston System, Houston, TX (US)

( * ) Notice: Subject to any disclaimer, the term of this patent is extended or adjusted under 35 U.S.C. 154(b) by 328 days.

(21) Appl. No.: 18/111,210

(22) Filed: Feb. 17, 2023

(65) Prior Publication Data

US 2023/0263771 A1 Aug. 24, 2023

Related U.S. Application Data

(60) Provisional application No. 63/312,351, filed on Feb. 21, 2022.

(51) Int. Cl.
*A61K 31/404* (2006.01)
*A61P 31/14* (2006.01)

(52) U.S. Cl.
CPC ............ *A61K 31/404* (2013.01); *A61P 31/14* (2018.01)

(58) Field of Classification Search
CPC ........ A61K 31/404; A61P 31/14; A61P 31/12; C07D 405/06
See application file for complete search history.

(56) References Cited

U.S. PATENT DOCUMENTS

| | | | | |
|---|---|---|---|---|
| 5,792,783 | A | 8/1998 | Tang et al. | |
| 2002/0102608 | A1 | 8/2002 | Sugen | |
| 2003/0119895 | A1 * | 6/2003 | Masferrer | A61K 31/42 514/339 |

FOREIGN PATENT DOCUMENTS

| | | |
|---|---|---|
| CN | 112175071 | 9/2020 |
| CN | 112159469 | 1/2021 |
| CN | 112175073 | 1/2021 |

(Continued)

OTHER PUBLICATIONS

Miyakawa K, Matsunaga S, Yokoyama M, et al. PIM kinases facilitate lentiviral evasion from SAMHD1 restriction via Vpx phosphorylation. Nat Commun. 2019;10(1):1844. Published Apr. 23, 2019. doi:10.1038/s41467-019-09867-7 (Year: 2019).*

(Continued)

*Primary Examiner* — Kortney L. Klinkel
(74) *Attorney, Agent, or Firm* — Shackelford, McKinley & Norton, LLP

(57) ABSTRACT

The invention relates to anti-viral compounds suitable for use in blocking virus entry into cells, and methods of blocking virus entry into cells by associating the cells with the anti-viral compounds. The associating may occur in vitro, or in vivo in a subject through administration of the anti-viral compounds to the subject. The invention also relates to methods of treating or preventing a viral infection in a subject by administering to the subject at least one anti-viral compound. The subject may be a human being suffering from or vulnerable to the viral infection. The virus may include a coronavirus, such as severe acute respiratory syndrome-related coronavirus 2 (SARS-COV-2).

18 Claims, 6 Drawing Sheets

(56) References Cited

FOREIGN PATENT DOCUMENTS

| | | | | |
|---|---|---|---|---|
| CN | 112210004 | | | 1/2021 |
| CN | 112225806 | | | 1/2021 |
| CN | 112409488 | | | 2/2021 |
| CN | 112521496 | | | 3/2021 |
| CN | 112574300 | | | 3/2021 |
| CN | 112661841 | | | 4/2021 |
| CN | 112724248 | | | 4/2021 |
| CN | 112794899 | | | 5/2021 |
| CN | 113004395 | | | 11/2021 |
| CN | 112625136 | | | 2/2022 |
| CN | 112940110 | | | 9/2022 |
| JP | 2005530781 | | | 10/2005 |
| JP | 2007084494 | A | * | 4/2007 |
| WO | 2007-084494 | | | 4/2007 |
| WO | WO2021158521 | | | 8/2021 |

OTHER PUBLICATIONS

Al-Saleem, Jacob. "Exploring knowledge graphs for COVID-19 drug discovery.", American Chemical Society (CAS), Jul. 29, 2021, www.cas.org/resources/cas-insights/exploring-knowledge-graphs-for-covid-19-drug-discovery. Accessed Jun. 17, 2025. (Year: 2021 ).*

Crawford et al., Protocol and Reagents for Pseudotyping Lentiviral Particles with SARS-CoV-2 Spike Protein for Neutralization Assays. Viruses 12, 1-15 (2020).

Lan et al., Structure of the SARS-CoV-2 spike receptor-binding domain bound to the ACE2 receptor. Nature, 581, pp. 215-220 (2020).

Walls et al., Structure, Function, and Antigenicity of the Sars-CoV-2 Spike Glycoprotein. 2020, Cell 180, 1-12.

Bakthavatsalam et al., Identification of Inhibitors of Integrin Cytoplasmic Domain Interactions With Syk. Front. Immunol., Jan. 8, 2021) 10.3389/fimmu.2020.575085.

Cherubin et al., Inhibition of Cholera Toxin and Other AB Toxins by Polyphenolic Compounds. PLoS One. Nov 9;11 (11), (2016).

E. Mahase et al. Covid-19: Pfizer's paxlovid is 89% effective in patients at risk of serious illness, company reports. BMJ 375, n273 (2021).

S. Collie, J. Champion, H. Moultrie, L.-G. Bekker, G. Gray Effectiveness of BNT162b2 Vaccine against Omicron Variant in South Africa. N Engl J Med 386, 494-496 (2022).

L. A. VanBlargan, et al. An infectious SARS-CoV-2 B.1.1.529 Omicron virus escapes neutralization by therapeutic monoclonal antibodies. Nat Med. (2022).

Y. W. Jian Shang, et al. Cell entry mechanisms of SARS-CoV-2. Proceedings of the National Academy of Sciences of the United States of America 117, 11727-11734 (2020).

Koshland, D. E. Application of a Theory of Enzyme Specificity to Protein Synthesis. 44, 98-104 (1958).

Investigational COVID-19 convalescent plasma: guidance for industry. United States Food and Drug Administration. (2020).

S. Su, L. Du & S. Jiang. Learning from the past: development of safe and effective COVID-19 vaccines. Nature Reviews Microbiology 19, 211-219 (2021).

National Center for Biotechnology Information (2022). PubChem Compound Summary for CID 2804154. Retrieved Oct. 26, 2022 from https://pubchem.ncbi.nlm.nih.gov/compound/2804154.

National Center for Biotechnology Information (2022). PubChem Compound Summary for CID 6150966. Retrieved Oct. 26, 2022 from https://pubchem.ncbi.nlm.nih.gov/compound/6150966.

National Center for Biotechnology Information (2022). PubChem Compound Summary for CID 5713746. Retrieved Oct. 26, 2022 from https://pubchem.ncbi.nlm.nih.gov/compound/5713746.

International Search Report for PCT/US2023/013287, mailed on Jun. 15, 2023.

Chemical Abstract compound, STN express, RN 186611-12-1 (Entered STN: Feb. 27, 1997).

* cited by examiner

SMALL MOLECULES THAT TREAT OR PREVENT VIRAL INFECTIONS

CROSS-REFERENCE TO RELATED APPLICATIONS

The present application claims the benefit of U.S. Provisional Patent Application No. 63/312,351, filed on Feb. 21, 2022. The entirety of the aforementioned application is incorporated herein by reference.

BACKGROUND

Viral infections present serious threats to public health and economic development. Moreover, current anti-viral treatments suffer from numerous limitations. Accordingly, a need exists for the development of novel anti-viral treatments.

SUMMARY

In some embodiments, the present disclosure pertains to a compound suitable for use in blocking virus entry into cells. In some embodiments, the compound includes, without limitation:

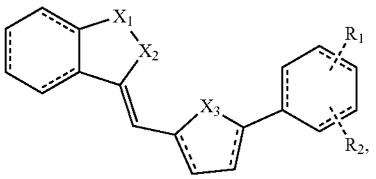

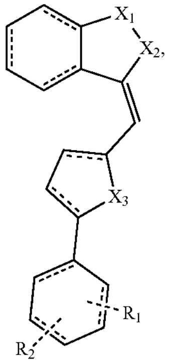

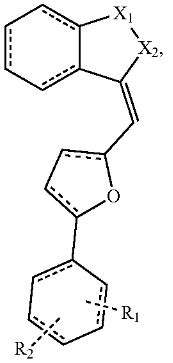

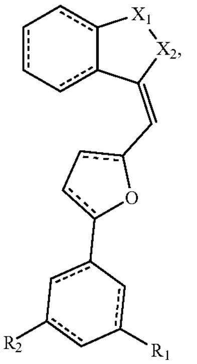

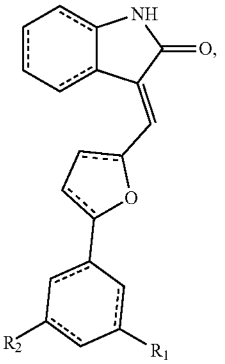

and derivatives thereof. In some embodiments, the compound includes the following structure:

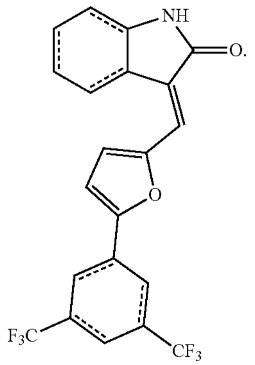

Additional embodiments of the present disclosure pertain to methods of blocking virus entry into cells. In some embodiments, such methods include associating the cells with at least one anti-viral compound of the present disclosure. In some embodiments, the associating occurs in vitro. In some embodiments, the associating occurs in vivo in a subject through administration of the at least one anti-viral compound to the subject.

Additional embodiments of the present disclosure pertain to methods of treating or preventing a viral infection in a subject by administering to the subject at least one anti-viral compound of the present disclosure. In some embodiments, the subject is a human being suffering from or vulnerable to the viral infection.

The methods of the present disclosure may be utilized to block the entry of various viruses into cells and treat or prevent various viral infections. For instance, in some embodiments, the virus includes a coronavirus, such as severe acute respiratory syndrome-related coronavirus 2 (SARS-CoV-2).

DESCRIPTION OF THE DRAWINGS

FIG. 2A illustrates the binding of the SARS-CoV-2 Spike protein (white surface) to the human ACE2 receptor complex. FIG. 2B shows CD04872SC bound on the surface of the Spike protein. FIG. 2C provides a three-dimensional structure of CD04872SC. FIG. 2D shows that CD04872SH has a predicted hydrogen-bond with backbone N of GLY169 and hydrophobic interactions with TYR116, TYR162, and TYR172.

FIG. 3A shows that HEK293 cells were transfected with a plasmid encoding a lentiviral backbone (genome) expressing a marker protein, a plasmid expressing Spike proteins of SARS-CoV-2 and its variants Delta and Omicron, and plasmids expressing the other proteins needed for virion formation (Tat, Gag-Pol, and Rev). The transfected cells produced lentiviral particles with SARS-CoV-2 Spikes on their surface. These viral particles can infect cells that overexpress the ACE2 receptor. The readout to measure the grade of viral infection is the green fluorescence of ZsGreen1 from infected cells. FIG. 3B shows the molecular structure of the interface of the receptor-binding domain (RBD) of the SARS-CoV-2 Spike protein (white surface) with the human ACE2 receptor (shaded surface). CD04872SC is predicted to bind on the face leading to potential disruption of the complex and where the CD04872SC is represented by Van der Waals (VDW) forces. FIG. 3C provides drug screening results of the selected top compounds (each at a concentration of 100 μM), which were evaluated for their antiviral activity against SARS-CoV-2, as defined by their percent infection inhibition. FIG. 3D shows the maximum antiviral activity against SARS-CoV-2, and its two major variants Delta and Omicron, for lead drug candidate CD04872SC. FIG. 3E shows the mean percent inhibition of viral infection and percent cell cytotoxicity of lead drug candidate CD04872SC in HEK293 cells expressing either the Spike protein of SARS-CoV-2, Delta, or Omicron with co-expression of the ACE2 receptor. In brief, HEK293 cells overexpressing the ACE2 receptor were pre-treated with the lead drug candidate CD04872SC for 1 hour. Then, 10 μl of the lentiviral suspensions expressing the Spike protein were added to the culture plates and incubated for 48 hours. After the incubation period, the green fluorescence of ZsGreen1 protein was measured with the plate reader Synergy 2 (BioTek) using the FITC channel. The mean percent inhibition and percent cytotoxicity is represented on each of the graph's left and right y-axis, respectively. For each of the three graphs, blue (i.e., circle dot) curves indicate the percent of infection inhibition and red (i.e., square dot) curves represent the percent of cytotoxicity. The results are expressed as mean±s.e.m. of three experiments performed in triplicate; each triplicate was averaged before calculating the s.e.m.

FIG. 4A provides a schematic representation of the viral neutralization concept of SARS-CoV2 by a small molecule. Targeting a specific region of the spike proteins makes it possible to neutralize the coronavirus by disrupting the binding between its spike protein and receptor ACE2. FIG. 4B provides the thermal stability of Delta variant pseudotyped lentiviral particles in the absence and presence of 500 μM CD04872SC. FIG. 4C shows a thermal shift assay performed with Omicron variant pseudotyped viral particles in the absence and the presence of 500 μM CD04872SC. FIG. 4D shows thermal stabilization of SARS-CoV2 pseudotyped viral particles in the presence of 500 μM CD04872SC. The results are expressed as the mean of three experiments performed in triplicate; each triplicate was averaged before calculating the s.e.m. Lead compound CD04872SC.

DETAILED DESCRIPTION

Figure 1A:
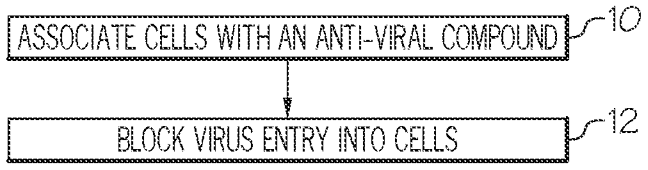
FIG. 1A illustrates a method of blocking viral entry into cells.

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that include more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Viral infections present serious threats to public health and economic development. For instance, the outbreak of coronavirus disease 2019 (COVID-19) caused by the severe acute respiratory syndrome coronavirus 2 (SARS-CoV-2/2019-nCoV) poses a serious threat to global public health and local economies. As of Oct. 2, 2022, over 618 million cases have been confirmed all over the world. Such large numbers of infected individuals and their associated mortality call for an urgent demand for effective, available, and affordable drugs to control and diminish the pandemic.

Furthermore, limitations exist in treating COVID-19. For instance, Pfizer's novel COVID antiviral treatment is useful only during the first three days of showing symptoms. Pfizer's PAXLOVID antiviral medication is not expected to be largely available for treating an enormous number of patients in a timely manner.

Additionally, the last SARS-CoV-2 variant (Omicron) is rapidly spreading and is more contagious than the original SARS-CoV-2 strain as well as the SARS-CoV-2 Delta variant. SARS-CoV-2 variants (Delta and Omicron) demonstrate how easily this virus can accommodate antigenic changes in its Spike (S) protein without loss of fitness. Particularly, the Omicron variant has stressed health care systems around the world.

In contrast to vaccines, which usually take several weeks to induce antibody production in immunized individuals, neutralizing small molecules may provide immediate protection against viral infection. Thus, antiviral small molecules may be suitable for people of all ages and be particularly suitable for high-risk populations and immunocompromised individuals who typically do not generate sufficient antibodies after vaccination.

Other available strategies for combatting viral infections include harvesting patient plasma from convalescent patients with potent neutralizing activities. However, the anti-viral efficacy of convalescent plasma remains uncertain. For instance, although the United States Food and Drug Administration has issued an emergency use authorization for the application of convalescent plasma to treat hospitalized patients with COVID-19, more randomized clinical trials are needed to determine the real efficacy and safety of convalescent plasma.

Another approach for combatting viral infections is by producing effective neutralizing monoclonal antibodies (mAbs) against the virus. However, the generation of mAbs in a cost-effective manner and at scale can be very challenging. For instance, most mAbs are produced in mammalian cells with relatively low productivity and thus high production costs.

In fact, manufacturing approaches that produce effective neutralizing antibodies with high expression yield at low cost are acutely needed. Moreover, many approaches to therapeutic treatment are in development with final outcomes remaining to be accessed.

As such a need exists to identify effective antiviral agents to combat viral infections. Numerous embodiments of the present disclosure address the aforementioned need.

In some embodiments, the present disclosure pertains to methods of blocking virus entry into cells. In some embodiments illustrated in FIG. 1A, such methods include associating the cells with an anti-viral compound (step 10) to result in the blocking of virus entry into the cells (step 12). In some embodiments, the association occurs in vitro. In some embodiments, the association occurs in vivo.

Figure 1B:
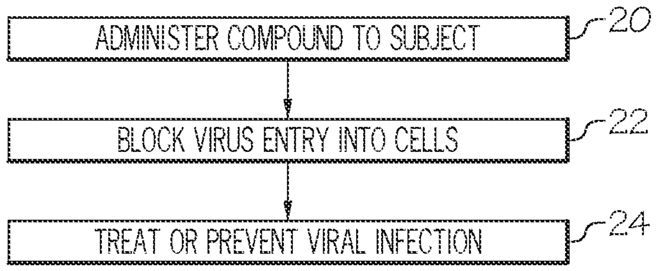
FIG. 1B illustrates a method of treating or preventing viral entry into subjects.
Figure 2A:
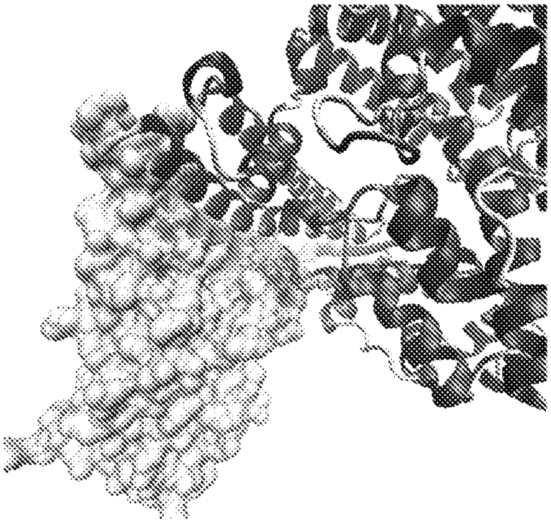
FIGS. 2A-2D provide a three-dimensional schematic and mechanistic representation of how compound CD04872SC disrupts the interface between the SARS-CoV-2 Spike protein and the ACE2 receptor.
Figure 2B:
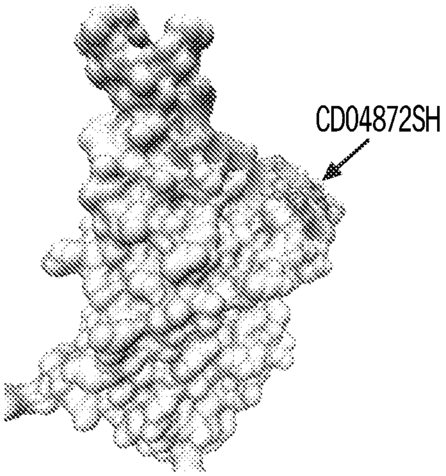
Figure 2C:
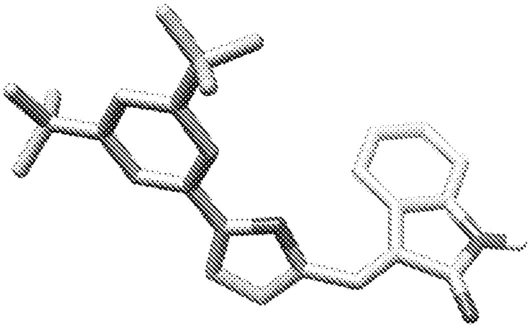
Figure 2D:
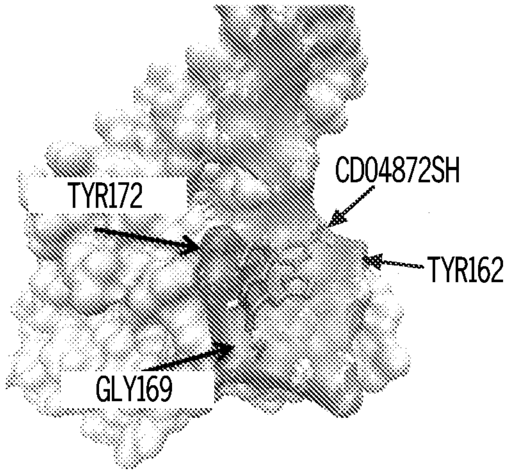

In some embodiments, the present disclosure pertains to methods of treating or preventing a viral infection in a subject. In some embodiments illustrated in FIG. 1B, such methods include administering an anti-viral compound to the subject (step 20) to result in the blocking of virus entry into the cells of the subject (step 22). This in turn results in the treatment and/or prevention of a viral infection in the subject (step 24).

Additional embodiments of the present disclosure pertain to compositions that include the anti-viral compounds of the present disclosure. Further embodiments of the present disclosure pertain to the use of the anti-viral compounds and compositions to block virus entry into cells for numerous purposes, such as treating or preventing viral infections.

As set forth in more detail herein, the present disclosure has numerous embodiments. For instance, various anti-viral compounds and compositions can be utilized to block the entry of various viruses into various cells. Moreover, the methods of the present disclosure can be utilized to treat or prevent numerous viral infections in numerous subjects.

Anti-Viral Compounds

The anti-viral compounds of the present disclosure can include numerous structures. For instance, in some embodiments, the anti-viral compounds can include one or more of the following structures:

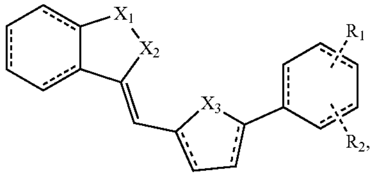

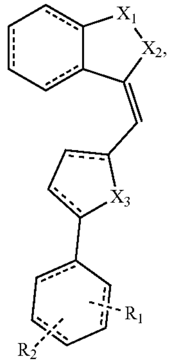

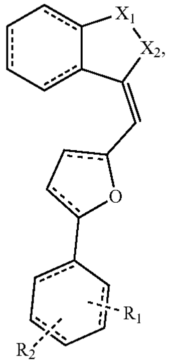

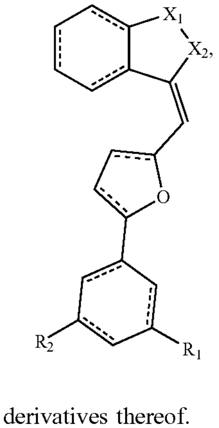

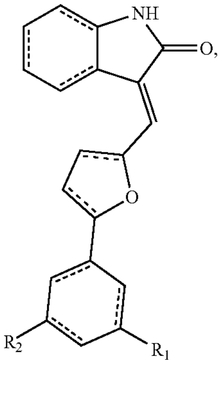

and derivatives thereof.

In some embodiments, each of $X_1$, $X_2$, and $X_3$ in the aforementioned structures can independently include, without limitation, NH, NOH, $NO_2H$, POH, $PO_2H$, CO, $CCl_2$, $CBr_2$, $CF_2$, O, S, and $CH_2$. In some embodiments, $X_1$ is NH, $X_2$ is CO, and $X_3$ is O.

In some embodiments, each of $R_1$ and $R_2$ in the aforementioned structures can independently include, without limitation, H, $CCl_3$, $CHCl_2$, $CH_2Cl$, $CF_3$, $CHF_2$, $CH_2F$, $CH_3$, alkyl groups, alkoxy groups, amine groups, carboxyl groups, aldehyde groups, ester groups, phenyl groups, silyl hydrides, silyl chlorides, silyl fluoride, silyl bromide, silyl ethers, silanols, siloles derivatives thereof, and combinations thereof.

In some embodiments, the anti-viral compounds of the present disclosure can include one or more of the following structures:

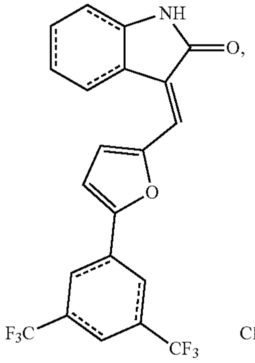

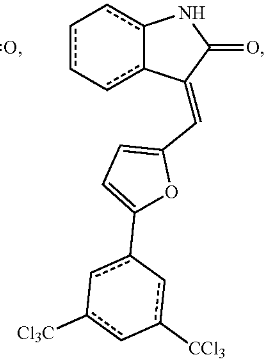

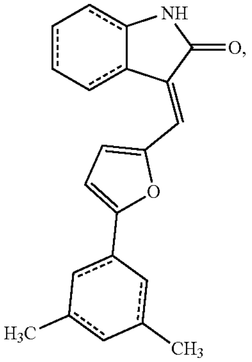

and derivatives thereof.

In some embodiments, the anti-viral compounds of the present disclosure include the following structure (also referred to as 3-({5-[3,5-di(trifluoromethyl)phenyl]-2-furyl}methylidene)indolin-2-one and CD04872SC):

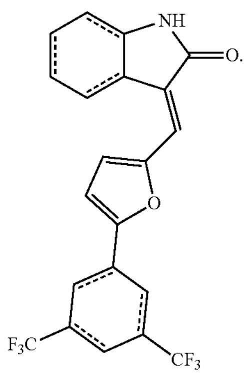

In some embodiments, the anti-viral compounds of the present disclosure include a derivative of an anti-viral compound of the present disclosure. In some embodiments, the derivative anti-viral compound includes one or more moieties derivatized with one or more functional groups. In some embodiments, the one or more functional groups include, without limitation, alkanes, alkenes, ethers, alkynes, alkoxyls, aldehydes, carboxyls, hydroxyls, hydrogens, sulfurs, phenyls, cyclic rings, aromatic rings, heterocyclic rings, linkers, methyl groups, hydrogen groups, tracing agents, derivatives thereof, and combinations thereof.

Anti-Viral Compositions

The anti-viral compounds of the present disclosure can be in various compositions. For instance, in some embodiments, the anti-viral compounds of the present disclosure are in therapeutic compositions.

The compositions of the present disclosure can be in various forms. For instance, in some embodiments, the compositions of the present disclosure are in the form of nasal sprays, eye drops, injectable suspensions, tablets, or combinations thereof. In some embodiments, the compositions of the present disclosure are in the form of nasal sprays.

In some embodiments, the compositions of the present disclosure can be in the form of particles. For instance, in some embodiments, the compositions of the present disclosure include lipid-based particles, carbon-based particles, metal-based particles, and combinations thereof. In some embodiments, the particles of the present disclosure are in the form of nanoparticles. In some embodiments, the anti-viral compounds of the present disclosure are encapsulated within the particles of the present disclosure.

In some embodiments, the compositions of the present disclosure also include one or stabilizers. In some embodiments, the stabilizers include, without limitation, anti-oxidants, sequestrants, ultraviolet stabilizers, and combinations thereof.

In some embodiments, the compositions of the present disclosure also include one or more surfactants. In some embodiments, the surfactants include, without limitation, anionic surfactants, cationic surfactants, zwitterionic surfactants, non-ionic surfactants, and combinations thereof.

In some embodiments, the compositions of the present disclosure also include one or more excipients. In some embodiments, the excipients include, without limitation, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, polyvinyl alcohol, anti-adherents, binders, coatings, colors, disintegrants, flavors, glidants, lubricants, preservatives, sorbents, sweeteners, or combinations thereof.

In some embodiments, the anti-viral compounds of the present may also include a delivery vehicle. In some embodiments, the delivery vehicle includes particles. In some embodiments, the particles include, without limitation, nanoparticles, liposomes, or combinations thereof. In some embodiments, the delivery vehicle includes liposomes. In some embodiments, the anti-viral compounds are encapsulated in the particles.

In some embodiments, the compositions of the present disclosure are in a form that is suitable for use as a nasal spray. In some embodiments, the compositions of the present disclosure are in a form that is suitable for use as an aerosol.

Prevention of Virus Entry into Cells

The anti-viral compounds of the present disclosure can be utilized to prevent the entry of various viruses into cells. For instance, in some embodiments, the virus includes a virus that is capable of entering cells through the angiotensin-converting enzyme 2 (ACE2) receptor. In some embodiments, the virus includes a virus that contains a Spike protein. In some embodiments, the Spike protein mediates viral entry into cells. In some embodiments, the virus includes a Spike protein or a similar cell entry protein that binds to one or more compounds of the present disclosure. In some embodiments, the virus includes, without limitation, coronaviruses, Influenza viruses, retroviruses (e.g., Human Immunodeficiency Virus), lentiviruses, or combinations thereof.

In some embodiments, the virus includes a coronavirus. In some embodiments, the coronavirus includes, without limitation, severe acute respiratory syndrome coronavirus (SARS-CoV), severe acute respiratory syndrome-related coronavirus (SARSr-CoV), human coronavirus 229E (HCoV-229E), human coronavirus NL63 (HCoV-NL63), human coronavirus OC43 (HCoV-0C43), human coronavirus HKU1 (HCoV-HKU1), Middle East respiratory syndrome-related coronavirus (MERS-CoV), severe acute respiratory syndrome-related coronavirus 1 (SARS-CoV-1), severe acute respiratory syndrome-related coronavirus 2 (SARS-CoV-2), or combinations thereof.

In some embodiments, the virus is SARS-CoV-2. In some embodiments, the virus is a delta variant of SARS-CoV-2. In some embodiments, the virus is an omicron variant of SARS-CoV-2.

Without being bound by theory, the anti-viral compounds of the present disclosure can block the entry of viruses into cells through numerous mechanisms. For instance, in some embodiments, the anti-viral compounds of the present disclosure block entry of a virus into cells by disrupting the binding of a viral cell entry protein to a cell receptor. In some embodiments, the viral cell entry protein is a Spike protein. In some embodiments, the cell receptor is an angiotensin-converting enzyme 2 receptor. In some embodiments, the disruption occurs when the anti-viral compounds of the present disclosure bind to a surface of the viral cell entry protein. In specific embodiments illustrated in FIGS. 2A-2D, the anti-viral compounds of the present disclosure block entry of a virus into cells by binding to a surface of viral Spike proteins and thereby disrupting the binding of the viral Spike proteins to angiotensin-converting enzyme 2 receptors.

Association of Anti-Viral Compounds and Compositions with Cells

The anti-viral compounds and compositions of the present disclosure can be associated with various types of cells. For instance, in some embodiments, the cells include, without limitation, endothelial cells, epithelial cells, or combinations thereof.

In some embodiments, the association of the anti-viral compounds and compositions of the present disclosure with cells occurs in vitro. In some embodiments, the association occurs in vivo. In some embodiments, the association occurs in vivo in a subject. In some embodiments, the association occurs in vivo in a subject through the administration of the compounds and compositions of the present disclosure to the subject.

In some embodiments, the administration occurs by oral administration, inhalation, subcutaneous administration, intravenous administration, intraperitoneal administration, intramuscular administration, intrathecal injection, intra-articular administration, topical administration, central administration, peripheral administration, aerosol-based administration, nasal administration, transmucosal administration, transdermal administration, parenteral administration, direct administration into airway epithelial cells, and combinations thereof. In some embodiments, the administration occurs by nasal administration. In some embodiments, the administration occurs by aerosol-based administration. In some embodiments, the administration occurs by direct administration into airway epithelial cells.

Subjects

The anti-viral compounds and compositions of the present disclosure may be administered to various subjects. For instance, in some embodiments, the subject is a mammal. In some embodiments, the subject is a human being. In some embodiments, the subject is an animal, such as a domesticated animal. In some embodiments, the domesticated animal includes, without limitation, cats, dogs, sheep, horses, cows, deer, or combinations thereof.

In some embodiments, the subject is suffering from a viral infection. In some embodiments, the subject is vulnerable to a viral infection.

In some embodiments, the anti-viral compounds, compositions and methods of the present disclosure can be utilized to treat a viral infection in a subject. In some embodiments, the anti-viral compounds, compositions, and methods of the present disclosure can be utilized to prevent a viral infection in a subject. In some embodiments, the viral infection is caused by a coronavirus, such as SARS-CoV-2.

The compounds and compositions of the present disclosure may be suitable for use in various applications. For instance, in some embodiments, the anti-viral compounds and compositions of the present disclosure may be suitable for use in treating or preventing a viral infection in a subject through the administration of the compounds or compositions to the subject in accordance with the methods of the present disclosure.

ADDITIONAL EMBODIMENTS

Reference will now be made to more specific embodiments of the present disclosure and experimental results that provide support for such embodiments. However, Applicant notes that the disclosure below is for illustrative purposes only and is not intended to limit the scope of the claimed subject matter in any way.

Example 1. A Small Molecule that In Vitro Neutralizes Infection of SARS-CoV-2 and its Most Infectious Variants, Delta, and Omicron In this Example, Applicant describes that the small molecule CD04872SC was able to neutralize SARS-CoV2 infection with a half-maximal effective concentration ($EC_{50}$) of 248 μM. Applicant was also able to observe that CD04872SC inhibited the infection of the SARS-CoV-2 variants; Delta ($EC_{50}$=152 μM) and Omicron ($EC_{50}$=308 μM). In some embodiments, these properties may define CD04872SC as a potential broad-spectrum candidate lead for the development of treatment of COVID-19.

Example 1.1. In-Silico Screening

Since the SARS-CoV-2 virus enters host cells via an interaction between its Spike protein and the host cell receptor angiotensin-converting enzyme 2 (ACE2), Applicant's goal was therefore to disrupt this interaction with a small molecule. To disrupt this protein-protein interaction, Applicant performed in-silico screening following a Cloud workflow implementation using Microsoft Azure and the University of Houston's Hewlett Packard Enterprise (HPE) Data Science Institute to execute a drug discovery workflow by using AutoDock Vina, GROMACS, and PySpark.

Candidate in-silico binding poses of compounds to the SARS-CoV-2 Spike protein were generated from over a million compounds from the Maybridge and ZINC libraries. Applicant selected the top 15 molecules, through in-silico screening, that disrupted the interaction between the Spike protein and the ACE2 receptor. Molecular dynamic simulations revealed that some of the compounds from these libraries had favorable interactions with the Spike protein's ACE receptor binding domain interface, leading to a potential neutralization of the SARS-CoV-2 infection. One of those compounds (CD04872SC) formed a close association between its amide carbonyl of the bicyclic indolin-2-one group and the backbone N of GLY169 (3.1 Å), and has hydrophobic interactions with TYR116, TYR162, and TYR172 (FIGS. 2A-D). The Lipinski and Muegge rules; MLOGP>4.15 (4.22 actual prediction) and XLOGP3>5 (5.73 actual prediction), respectively, are used as guidelines for the drug-likeness of initial leads. Applicant's compound slightly exceeds these guidelines, but it remained a viable candidate.

Figure 3A:
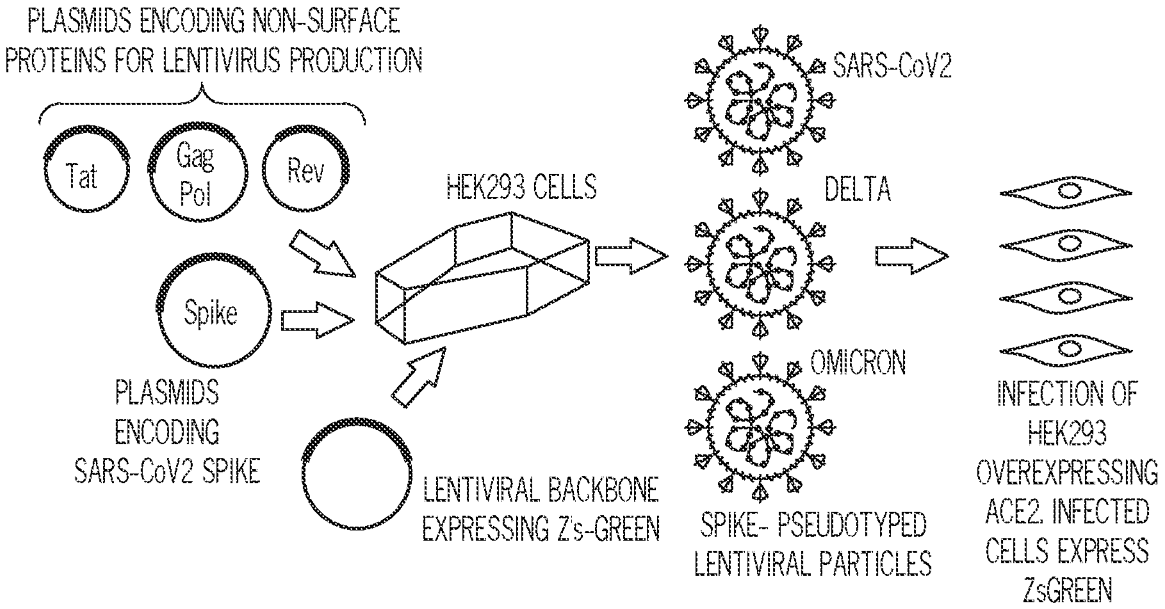
FIGS. 3A-3E illustrate a lentiviral system approach and antiviral activities of the test drugs against SARS-CoV-2 and its variants Delta and Omicron in vitro.

Example 1.2. Inhibition of In Vitro Infection of SARS-CoV2, Delta, and Omicron To corroborate Applicant's in-silico data, cell infection and viability assays were carried out to measure the effects of these top 15 compounds on cell infection rates and cell cytotoxicity. HEK293 cells (ATCC-1586) overexpressing the ACE2 receptor were infected with lentiviruses that express the Spike protein found in SARS-CoV-2 (FIG. 3A).

Figure 3B:
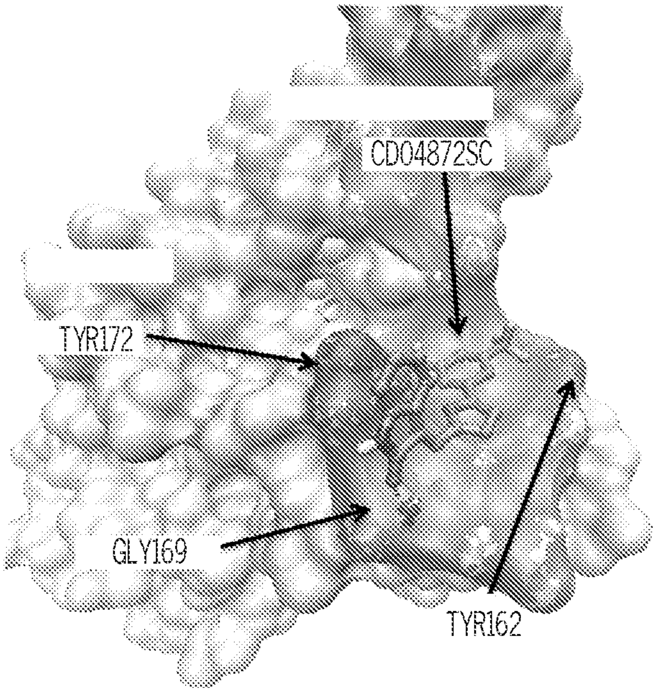

Thereafter, in the presence of the compounds identified from the in-silico data, Applicant measured the green fluorescence intensity of ZsGreen1 protein 48 hours post-infection. Next, this assay was repeated by independently expressing the Spike protein's variants, Delta and Omicron, also in HEK293 cells overexpressing the ACE2 receptor (FIG. 3A). These in vitro SARS-CoV-2 Spike protein and ACE2 receptor co-expression cellular studies confirmed the in-silico molecular strategy that aimed at disrupting the interface of the SARS-CoV-2 Spike protein and ACE2 receptor by docking a small molecule at the receptor-binding site of the Spike protein (FIG. 3B).

Figure 3C:
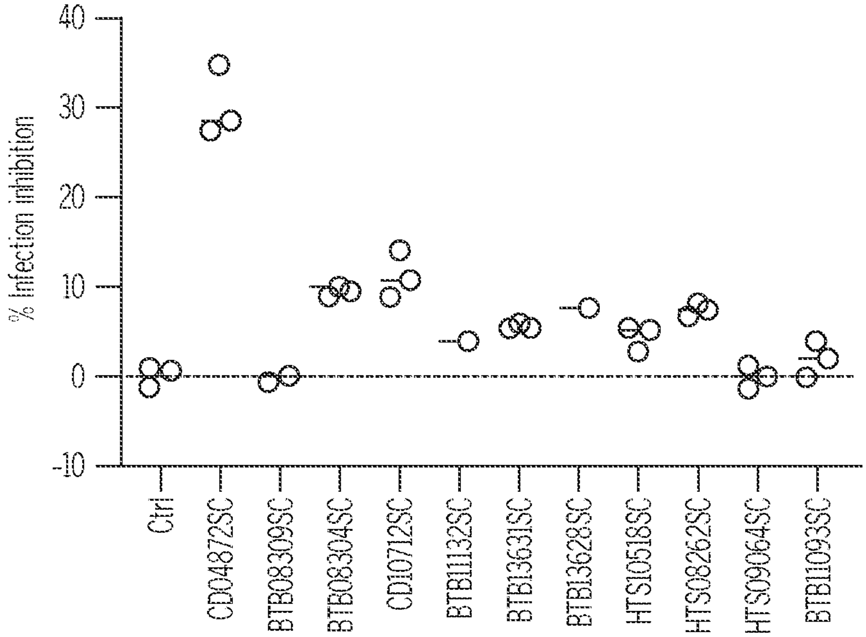

Next, Applicant performed infection inhibition drug screening and cell cytotoxicity assays. From the drug screening assays, Applicant identified CD04872SC as the lead compound (FIG. 3C). Next, Applicant validated this lead compound by determining its infection rate.

Figure 3D:
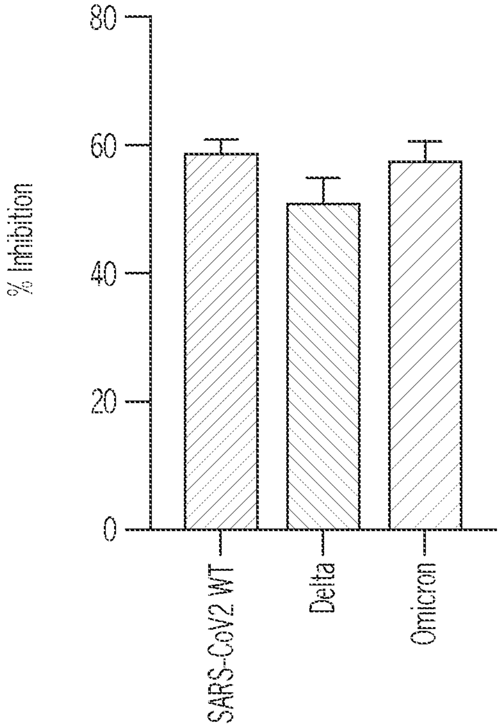
Figure 3E:
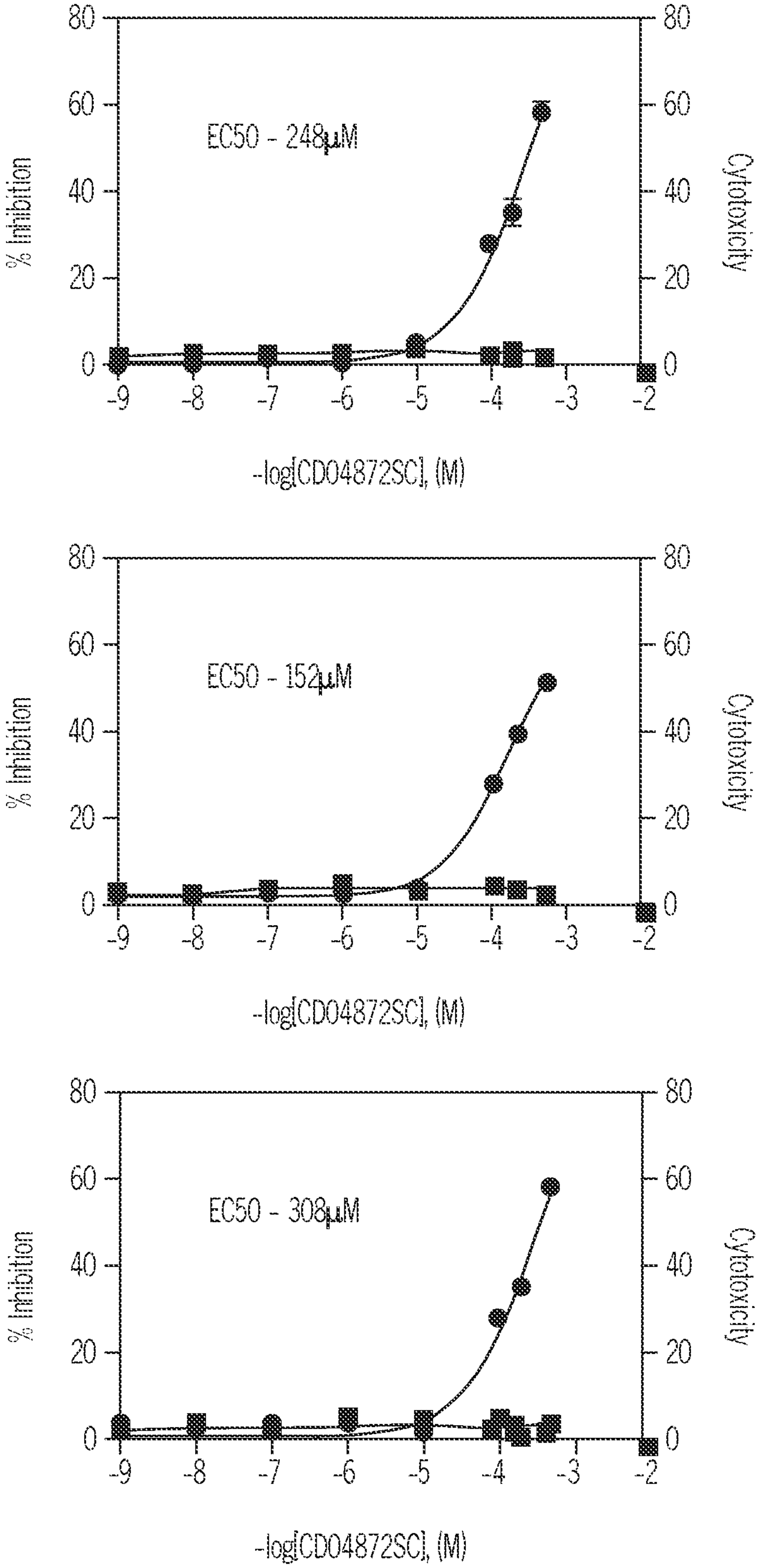

Applicant found that CD04872SC showed a half-maximal effective concentration (EC50)=248 μM; the concentration capable of reducing the viral infection of the cells expressing SARS-CoV-2 Spike protein (FIG. 3D). Furthermore, Applicant observed that CD04872SC also inhibited the infection of the SARS-CoV-2 variants; Delta (EC50=152 μM) and Omicron (EC50=308 μM) (FIG. 3D). Finally, the CD04872SC lead compound was tested at various concentrations in cell cytotoxicity assays using the PrestoBlue™ Cell Viability Reagent (Life Technologies Cat. No. A13261) kit and found that CD04872SC was without major cell cytotoxicity within the indicated concentrations (FIG. 3E).

Example 1.3. CD04872SC Inhibits Viral Infection by Direct Binding to the Spike Protein of SARS-CoV2, Delta, and Omicron A Protein Thermal Shift assay was developed for the analysis of viral particles melting point fluorescent readings directly from a BIO-RAD real-time PCR instrument. Viral particle stability changed in the presence of CD04872SC. Real-time melt experiments were used to demonstrate the direct binding between CD04872SC and the spike protein of each SARS-CoV2 variant. The presence of CD04872SC binding the Spike protein is evaluated as changes in the fluorescence profiles (melt curves) as shown in FIGS. 4A-D. This was converted to a $T_m$ which is calculated based on the inflection point of the melt curves.

Figure 4A:
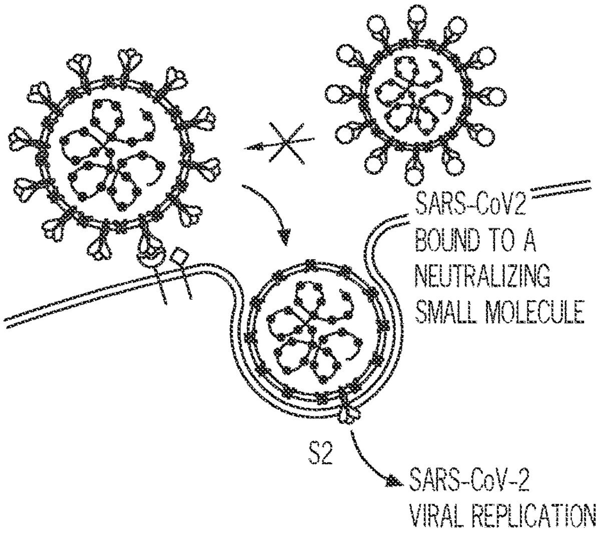
FIGS. 4A-4D illustrate that CD04872SC binds to the spike protein of SARS-CoV2, Delta, and Omicron.

Without being bound by theory, the potential mechanisms of action of CD04872SC for the prevention and treatment of SARS-CoV-2 infection are described in FIG. 4A. In the absence of specific drugs, SARS-CoV2 binds the ACE2 receptor through the receptor binding domain (RBD) in the S1 subunit, mediating viral entry and subsequent membrane fusion. In the presence of CD04872SC targeting and binding to the SARS-CoV2 RBD, interaction with the ACE2 receptor is blocked and membrane fusion is inhibited.

Figure 4B:
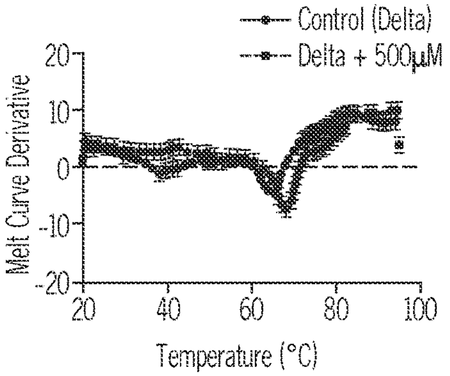
Figure 4C:
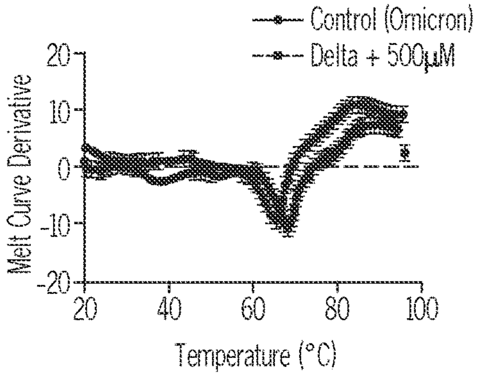
Figure 4D:
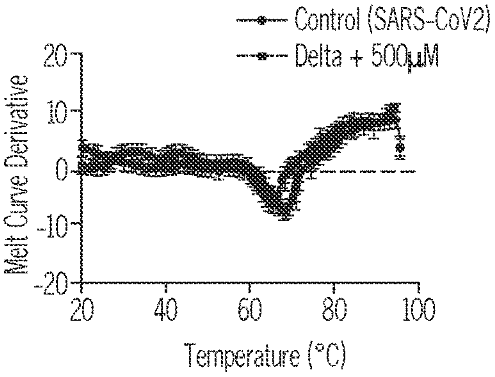

To demonstrate the binding between CD04872SC and the spike proteins of each variant, Applicant performed a Thermal Shift Assay (FIGS. 4B-D). Thermal Shift Assays measure changes in the thermal denaturation temperature, serving as an indicator of the stability of a protein under varying conditions such as when bound by a drug, buffer pH, ionic strength, redox potential, or sequence mutation. The method for measuring spike protein thermal shifts was based on differential scanning fluorimetry (DSF) or thermofluor, which utilizes a specialized fluorogenic dye. The binding of low molecular weight ligands can increase or decrease the thermal stability of a protein.

As shown in FIGS. 4B-4D, Applicant observed a difference of about 3 Celsius degrees of stability in the presence of CD04872SC in the SARS-CoV2 viral suspensions versus its absence. Moreover, Applicant was able to observe the same stabilizing tendency for the variants Delta and Omicron (FIGS. 4B-4D).

Example 1.4. Discussion

Applicant's findings reveal that CD04872SC is effective in inhibiting the SARS-CoV-2 Spike protein binding to the ACE2 receptor; including, its most infectious variants (Delta and Omicron) in functional in vitro assays. These data were developed from the application of large screen computational screening of small molecule databases for hits against the Spike protein target and ranked for evaluation in cell-based assays. A SARS-CoV-2 specific reporter system was developed by Applicant's group and used to confirm that the small molecule lead, CD0487SC, did prevent the binding with the ACE receptor and will form the foundations of a drug development effort to find derivatives and enhancements to evolve CD0487SC into a clinically viable drug candidate. In summary, this Example suggests that CD04872SC might be the starting point for the potential treatment of severe COVID-19 and mortality in the era of Omicron.

Example 1.5. Molecular Modeling

Following well-established protocols in summary; structures (PDB 6M0J, 6VXX, and 6VYB) were used to prepare models of the SARS-CoV-2 Spike protein RBD and the ACE2 receptor (*Cell* 180, 1-12 (2020) and *Nature* 581, 215-220 (2020)). CD04872SC was initially expanded into its 3D minimized structure using BALLOON 3-1.6.6 and then processed with PRODRG4 to build topology files. Both the spike protein and the ligand were prepared for docking analysis using AUTODOCK-TOOLS and AUTODOCK_VINA 1.1.2. Docking for each of the millions of compounds evaluated from the Maybridge and ZINC library was completed with exhaustiveness set to 100 and the top 20 poses evaluated in each tranche and evaluated in both the Microsoft Azure Cloud and our university servers.

Example 1.6. Lentivirus-Mediated Expression of the Spike Protein of SARS-CoV-2

Manipulations took place in a biosafety cabinet. HEK293 cells were transfected with the plasmids containing SARS-CoV-2, Wuhan-Hu-1 (GenBank: NC_045512), spike-pseudotyped lentiviral kit (NR-52948, from Bei Resources) designed to generate pseudotyped lentiviral particles expressing the spike (S) glycoprotein gene, as well as luciferase (Luc2) and ZsGreen. Seventy-two hours after transfection, the medium was collected in a 50 ml tube and stored at −80° C. for further applications. This protocol only requires Biosafety Level 1 (BSL1) conditions and the viruses used in this protocol were replication-defective.

The plasmid expressing the human ACE2 gene was acquired from Addgene (Cat. No. 1786). The plasmid expressing the Delta Spike Protein (Cat. No. VG40819-UT) was acquired from Sino Biological. The plasmid expressing the Omicron Spike Protein (Cat. No. MC_0101274) was acquired from GenScript.

The following describes the detailed protocol for the Generation of Pseudo typed Lentiviral Particles by transfecting HEK293. Applicant used the following protocol from Crawford and colleagues (*Viruses* 12, 1-15 (2020)). In brief, Applicant seeded HEK293 cells in a DMEM High Glucose growth medium so that they would be 70% confluent the next day. For a six-well plate, this was equivalent to $8\times10^5$ cells per well. The next morning following 12-16 hours after seeding, the cells were transfected with the plasmids required for lentiviral production. Applicant transfected the cells using Viafect (Promega Corporation, Cat. No. E4982) following the manufacturer's instructions and using the following plasmid mix per well of a six-well plate (plasmid amounts were adjusted for larger plates): 1 μg of lentiviral backbone: ZsGreen (NR-52520) or the Luciferase-IRES-ZsGreen (NR-52516) backbone; 0.22 μg each of plasmids: HDM-Hgpm2 (NR-52517), pRC-CMV-Rev1b (NR-52519), and HDM-tat1b (NR-52518); 0.34 μg viral entry protein: either SARS-CoV-2 Spike (NR-52513, NR-52514); At 60 hours post-transfection, the virus was collected by harvesting the supernatant from each well and filtering it through a 0.45 μm SFCA low protein-binding filter. The viruses were then concentrated by using Lenti-X™ (Cat. No. 631231, Takara Bio Inc). The virus was resuspended in 200 μl of PBS and followed by the viral suspensions stored frozen at −80° C.

Example 1.7. Neutralization Assay

Applicant seeded a poly-L-lysine-coated 96-well plate with $4\times10^4$ HEK293 cells per well in 100 μL DMEM High Glucose. The following morning, Applicant transfected the cells with Viafect (Promega, Cat. No. E4982) and 100 ng of ACE2 plasmid per well. Applicant let the ACE2 receptor express in the cells for 36 hours after transfection. Then, Applicant pretreated the cells with different concentrations of the different compounds and incubated the cells for 1 hour. Thereafter, Applicant used 10 μL concentrated viral suspension to infect the cells in the 96 well plate. Applicant incubated at 37° C. for 36 hours before measuring the green fluorescence (530/30 filter to detect ZsGreen in the FITC channel). For Applicant's analysis, Applicant first subtracted out the background signal (average of the "virus only" and "virus+HEK293" wells) and then calculated the "maximum infectivity" for each plate as the average signal from the wells without the drug ("virus+cells" wells). Applicant then calculated the "fraction infectivity" for each well, as the green fluorescence reading from each well was divided by the "maximum infectivity" for that plate. For the curves shown in FIGS. 3A-E, Applicant then fit and plotted the fraction infectivity data using Prism 7. This program fits a three-parameter Hill curve to determine the potency of neutralization (equation 1), with the top baseline being a free parameter and the bottom baseline fixed to zero.

$$\text{Response} = \text{Bottom} + \frac{\text{Top} - \text{Bottom}}{1 + 10^{(logEC_{50} - log[A])}} \qquad (1)$$

Example 1.8. Thermal Shift Assay

To monitor the SARS-CoV2 spike protein unfolding, the Protein Thermal Shift Dye was used. Protein Thermal Shift Dye is an environmentally sensitive dye. The unfolding process exposes the hydrophobic region of proteins and results in a large increase in fluorescence, which is used to monitor the protein-unfolding transition. The thermal shift assay was conducted in the CFC OPUS 384 Real-Time PCR System (Bio-Rad, Hercules, CA), originally designed for PCR. The system contains a heating/cooling device for accurate temperature control and a charge-coupled device (CCD) detector for simultaneous imaging of the fluorescence changes in the wells of the microplate. Solutions of 20 μl were prepared as follows: 5 μl of Thermal Shift Assay buffer+12.5 μl of viral particles in the absence or the presence of CD04872SC+2.5 μl Diluted Thermal Shift Dye (8×) were added to each well of the 384-well PCR plate. The final concentration of CD04872SC was 500 μM. The plate was heated from 20 to 95° C. with a heating rate of 0.5° C./min. The fluorescence intensity was measured using the ROX channel.

Example 1.9. Statistics and Reproducibility

The results were analyzed using the Prism 7 application (Graph Pad Software Inc., San Diego, CA). Dose-response curves were fitted using equation 1. In equation 1, the bottom and top are the lower and upper plateaus, respectively, of the concentration-response curve and where [A] is the molar concentration of the agonist and $EC_{50}$ is the molar concentration of the agonist required to generate a response halfway between the top and the bottom.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of treating or preventing a viral infection in a subject, said method comprising:

administering to the subject at least one compound, wherein the at least one compound is selected from the group consisting of:

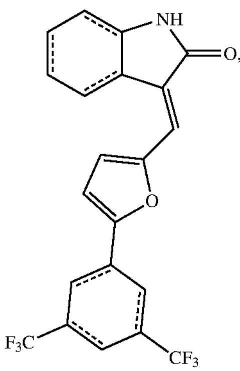
,
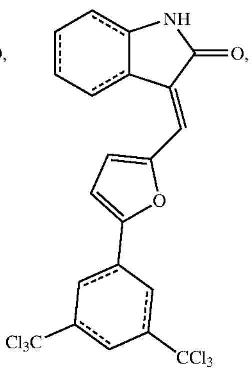
,
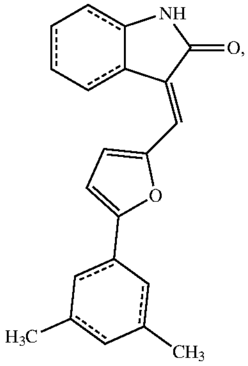
, or combinations thereof.

2. The method of claim 1, wherein the compound comprises the following structure:

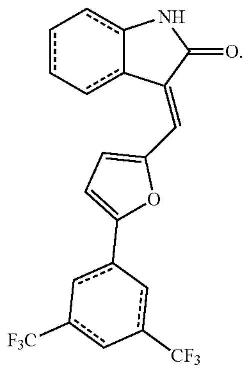

3. The method of claim 1, wherein the compound is in a composition.

4. The method of claim 3, wherein the composition is in a form selected from the group consisting of nasal sprays, aerosols, eye drops, injectable suspensions, tablets, or combinations thereof.

5. The method of claim 3, wherein the composition is in an aerosol form.

6. The method of claim 1, wherein the administering occurs by a method selected from the group consisting of oral administration, inhalation, subcutaneous administration, intravenous administration, intraperitoneal administration, intramuscular administration, intrathecal injection, intra-articular administration, topical administration, central administration, peripheral administration, aerosol-based administration, nasal administration, transmucosal administration, transdermal administration, parenteral administration, direct administration into airway epithelial cells, and combinations thereof.

7. The method of claim 1, wherein the administration comprises nasal administration.

8. The method of claim 1, wherein the administration comprises aerosol-based administration.

9. The method of claim 1, wherein the administration comprises direct administration into airway epithelial cells.

10. The method of claim 1, wherein the subject is a human being.

11. The method of claim 1, wherein the subject is suffering from the viral infection.

12. The method of claim 1, wherein the subject is vulnerable to the viral infection.

13. The method of claim 1, wherein the method is utilized to prevent the virus from infecting the subject.

14. The method of claim 1, wherein the method is utilized to treat the subject from an infection by the virus.

15. The method of claim 1, wherein the method is utilized to treat and prevent the viral infection.

16. The method of claim 1, wherein the virus causing the viral infection comprises a virus containing a Spike protein, a cell entry protein that binds to the at least one compound, or combinations thereof.

17. The method of claim 1, wherein the virus causing the viral infection comprises a coronavirus, an influenza virus, a retrovirus, a lentivirus, or combinations thereof.

18. The method of claim 1, wherein the virus causing the viral infection comprises a coronavirus selected from the group consisting of severe acute respiratory syndrome coronavirus (SARS-COV), severe acute respiratory syndrome-related coronavirus (SARSr-COV), human coronavirus 229E (HCoV-229E), human coronavirus NL63 (HCoV-NL63), human coronavirus OC43 (HCoV-OC43), human coronavirus HKU1 (HCoV-HKU1), Middle East respiratory syndrome-related coronavirus (MERS-COV), severe acute respiratory syndrome-related coronavirus 1 (SARS-COV-1), severe acute respiratory syndrome-related coronavirus 2 (SARS-COV-2), or combinations thereof.

* * * * *